US012751984B2

(12) United States Patent
Decherf et al.

(10) Patent No.: US 12,751,984 B2
(45) Date of Patent: Oct. 6, 2026

(54) COMPOSITION CONTAINING A YEAST FOR PREVENTING SIMPLE AND/OR RECURRING CYSTITIS

(71) Applicant: LESAFFRE ET COMPAGNIE, Paris (FR)

(72) Inventors: Amélie Decherf, Bondues (FR); Nathalie Ballet, Marcq-en-Baroeul (FR)

(73) Assignee: LESAFFRE ET COMPAGNIE, Paris (FR)

(*) Notice: Subject to any disclaimer, the term of this patent is extended or adjusted under 35 U.S.C. 154(b) by 476 days.

(21) Appl. No.: 17/616,409

(22) PCT Filed: May 29, 2020

(86) PCT No.: PCT/EP2020/065046
§ 371 (c)(1),
(2) Date: Dec. 3, 2021

(87) PCT Pub. No.: WO2020/245057
PCT Pub. Date: Dec. 10, 2020

(65) Prior Publication Data
US 2022/0233618 A1 Jul. 28, 2022

(30) Foreign Application Priority Data
Jun. 4, 2019 (FR) ........................................ 1905888

(51) Int. Cl.
*A61K 36/064* (2006.01)
*A23L 33/14* (2016.01)
(Continued)

(52) U.S. Cl.
CPC ............ *A61K 36/064* (2013.01); *A23L 33/14* (2016.08); *A61P 13/10* (2018.01); *A61P 31/04* (2018.01)

(58) Field of Classification Search
CPC ......... A61K 36/064; A23L 3/14; A23L 33/14; A23L 33/145; A61P 13/10; A61P 31/04
See application file for complete search history.

(56) References Cited

U.S. PATENT DOCUMENTS 9,474,292 B1 * 10/2016 Morrison ............... A23K 1/008
2007/0244069 A1 * 10/2007 Katz .................... A61K 31/715
514/61
(Continued)

FOREIGN PATENT DOCUMENTS

FR 2906109 B1 9/2009
WO 2009103884 A2 8/2009
(Continued)

OTHER PUBLICATIONS

Yoon et al. Risk factors for recurrent cystitis following acute cystitis in female patients, 2013, Journal of Infectious Chemotherapy, 2013, 19: 727-731 (Year: 2013).*
(Continued)

*Primary Examiner* — Samira J Jean-Louis
*Assistant Examiner* — Amelia Nicole Dickens
(74) *Attorney, Agent, or Firm* — Maier & Maier, PLLC

(57) ABSTRACT

A composition containing at least one yeast for the prevention of simple and/or recurring cystitis such as cystitis caused by uropathogenic *Escherichia coli* bacteria. The yeast may be in the form of a live yeast, a dead yeast, yeast cell walls, purified fractions of yeast cell walls or mixtures thereof.

10 Claims, 3 Drawing Sheets

(51) Int. Cl.
*A61P 13/10* (2006.01)
*A61P 31/04* (2006.01)

(56) References Cited

U.S. PATENT DOCUMENTS

| | | | | |
|---|---|---|---|---|
| 2009/0092641 | A1* | 4/2009 | Courie | A61K 31/715 424/278.1 |
| 2010/0303778 | A1* | 12/2010 | Simon | A61P 1/00 426/62 |
| 2015/0257599 | A1* | 9/2015 | Ng et al. | A47J 42/14 |
| 2020/0113954 | A1* | 4/2020 | Chiozza | A61K 36/064 |

FOREIGN PATENT DOCUMENTS

| | | | |
|---|---|---|---|
| WO | 2014009656 | A1 | 1/2014 |
| WO | 2015189337 | A1 | 12/2015 |
| WO | WO-2016159859 | A1 * | 10/2016 |

OTHER PUBLICATIONS

Sen, A. (Recurrent cystitis in non-pregnant women, 2008, Clinical Evidence, 7:801, 1-10) (Year: 2008).*

Torella et al.Intravesical therapy in recurrent cystitis: a multi-center experience, 2013, Journal of Infectious Chemotherapy, 19:920-925 (Year: 2013).*

Sihra et al. Nonantibiotic prevention and management of recurrent urinary tract infection, 2018, Nature, 15: 750-776) (Year: 2018).*

McKechnie (Recurrent cystitis in women, 2023) (Year: 2023).*

Alaryan et al. Overview of the causes and types of recurrent cystitis, 2022. International Journal of Community Medicine and Public Health, 10:3867-3872 (Year: 2022).*

Outwater et al. (2016, Chapter on Disease Prevention: An Overview, In Book: International Encyclopedia of Public Health (pp. 338-349), Second edition, Publisher: Oxford Academic Press, Editors: Quah et al.) (Year: 2016).*

Murray, D. "Health Benefits of Brewer's Yeast" verywellHealth website, updated on Sep. 3, 2022 and accessed at www.verywellhealth.com/brewers-yeast-benefits-431836 on May 4, 2024.*

Biedermann et al. "Bilberry ingestion improves disease activity in mild to moderate ulcerative colitis—An open pilot study", May 2013, Journal of Crohn's and Colitis, vol. 7, Issue 4, p. 271-279. (Year: 2013).*

Correction to Biedermann et al., last updated Jan. 2, 2024, Journal of Crohn's and Colitis, vol. 17, Issue 1, Jan. 2023, p. 149 (Year: 2024).*

Roussel et al. "Anti-infectious properties of the probiotic *Saccharomyces cerevisiae* CNCM I-3856 on enterotoxigenic *E. coli* (ETEC) strain H10407", May 25, 2018, Applied Microbiology and Biotechnology, vol. 102, p. 6175-6189. (Year: 2018).*

International Search Report (with English translation) and Written Opinion (with Machine translation) issued on Aug. 27, 2020 in corresponding International Application No. PCT/EP2020/065046, 15 pages.

Kauffman et al., "Candida Urinary Tract-Infections-Diagnosis"; Clinical infectious diseases; 2011; pp. S452-S456.

Madden-Fuentes et al., "Efficacy of Fluoroquinolone/Probiotic Combination Therapy for Recurrent Urinary Tract Infection in Children: A Retrospective Analysis"; Clinical Therapeutics; 2015; vol. 37, No. 9; pp. 2143-2147.

Khan, et al. "Update on Associated Risk Factors, Diagnosis, and Management of Recurrent Urinary Tract Infections in Children"; Journal of the Pediatric Infectious Diseases Society; 2019; vol. 8, No. 2; pp. 152-159.

Duane et al., "COSUTI: A Protocol for the Development of a Core Outcome Set (COS) for Interventions for the Treatment of Uncomplicated Urinary Tract Infection (UTI)in Adults", Trials, The Authors, BMC, 2019, vol. 20, No. 106, 6 pages.

Colgan et al., "Diagnosis and Treatment of Acute Uncomplicated Cystitis", American Family Physician, American Academy of Family Physicians, Oct. 1, 2011, vol. 84, No. 7, 6 pages.

Monard et al., "Fréquence des Colibacilles Adhérents Dans une Population de Pyélonéphrite Aiguë et Dans Une Population de Cystite Aiguë [Frecuencia de los colibacilos adherentes en una poblacion de pielonefritis aguda y en una poblacion de cistitis aguda]", Progres en Urologie, 1993, vol. 3, pp. 583-589, with partial English translation.

Rezuqi et al., "Inhibition Activity of *Saccharomyces boulardii* and *Lactobacillus acidophilus* Against Pathogenic *E.coli* Isolates from Recurrent Urinary Tract Infection in Women In Vitro", Baghdad Science Journal, 2014, vol. 11, No. 1, Article 4, 37 pages.

Lee et al., "A Case Report of *Saccharomyces cerevisiae* Fungemia in a Premature Infant Following Probiotic Treatment", Annals of Clinical Microbiology, Korea Society of Clinical Microbiology, Sep. 2020, vol. 23, No. 3, pp. 215-218.

European Food Safety Authority, "Scientific Opinion on the Substantiation of a Health Claim Related to *Saccharomyces cerevisiae* Var. *Boulardii* CNCM 1-3799 and Reducing Gastro. Intestinal Discomfort Pursuant to Article 13(5) of Regulation (EC) No 1924/2006", EFSA Journal, European Food Safety Authority, Jul. 17, 2012, vol. 10, No. 7, 9 pages.

Cetin et al., "The Usefulness of '*Saccharomyces boulardii*' In Treatment and Prophylaxis of Urinary Tract Infection In Children", Abstract P389, Pediatr Nephrol, Springer, Sep. 2014, vol. 29, 2 pages.

Akil et al., "Influence of Oral Intake of *Saccharomyces boulardii* on *Escherichia Coli* in Enteric Flora", Pediatr Nephrol, IPNA, Apr. 20, 2006, vol. 21, 1 page.

Jann et al., "*Escherichia coli* Adhesion to *Saccharomyces cerevisiae* and Mammalian Cells: Role of Piliation and Surface Hydrophobicity", Infection and Immunity, May 1981, vol. 32, No. 2, 6 pages.

Korhonen et al., "Binding Specificity of Piliated Strains of *Escherichia coli* and *Salmonella typhimurium* to Epithelial Cells, Saccharomyces Cerevisiae Cells, and Erythrocytes", Infection and Immunity, May 1981, vol. 32, No. 2, 9 pages.

Kello, "Oral Vial with Plunger and Tear Off Cap (VPTC) is an Alternative Dosage Form for Dietary Supplements", Journal of Critical Reviews, The Authors, Innovare Academic Science Pvt Ltd., 2016, vol. 3, No. 4, 6 pages.

Saoud et al., "*Saccharomyces cerevisiae*, is a Yeast Cell More and More Involved in Urinary Tract Infections: About 3 Cases", Pan African Medical Journal, Mar. 3, 2020, 4 pages.

Elkhihal et al., "Urinary infection by *Saccharomyces cerevisiae*: Emerging yeast?", Journal de Mycologie Medicate, Elsevier Masson SAS, Oct. 2, 2015, vol. 25, 3 pages with partial English translation.

Opposition issued Jul. 29, 2025, in European application 20733692.6, 14 pages.

* cited by examiner

[Fig. 1]
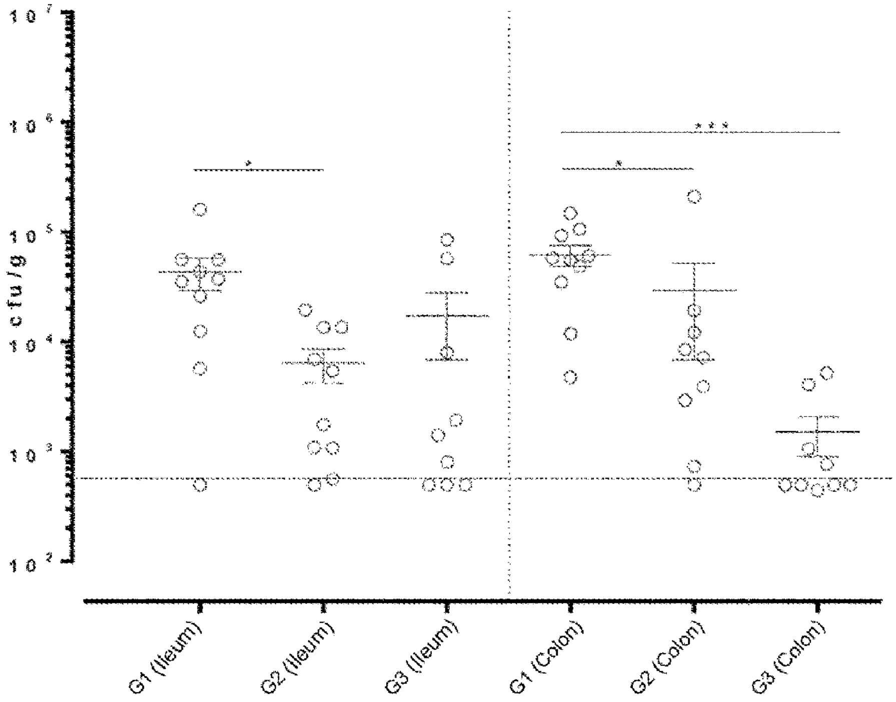
[Fig. 2]
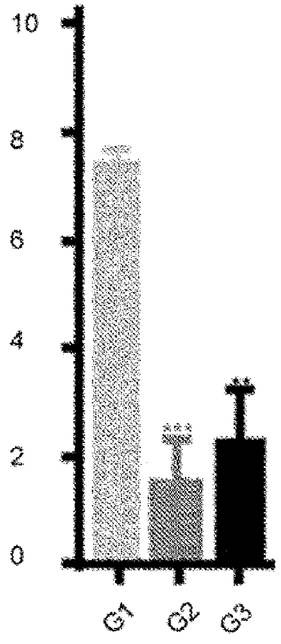

[Fig. 3]
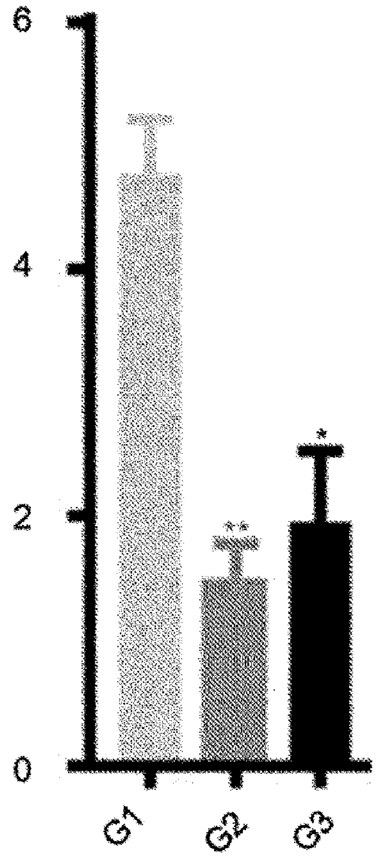

[Fig. 4]
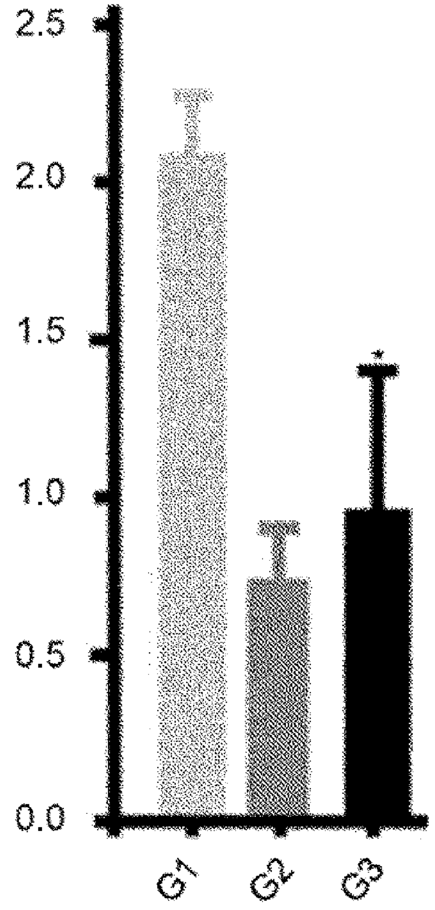

COMPOSITION CONTAINING A YEAST FOR PREVENTING SIMPLE AND/OR RECURRING CYSTITIS

FIELD

The present invention relates to the field of urinary infections. It relates more particularly to a yeast for preventing simple cystitis and/or recurrent cystitis.

BACKGROUND

Urinary infections are the main cause of bacterial infection throughout the world. Sex and age are important risk factors for contracting a urinary infection. In general, and for all age groups taken together, women are more at risk of developing a urinary infection. Thus, more than 50% of women will have a urinary infection at least once during their lifetime and up to 30% of these women will suffer from recurrent urinary infections. Moreover, 10 to 15% of men will suffer from at least one infectious episode.

In the hospital environment, urinary infections represent the second commonest nosocomial infection, after pulmonary infections. The commonest cause is application of a urinary catheter.

Urinary infections may also be classified in respect of complications. Urinary infections are said to be uncomplicated when there are no abnormalities of structure or of function of the urinary tract, there is no infection at the renal level (no nephropathy) and there is absence of comorbidity (other diseases such as diabetes, hypertension, etc.). A urinary infection is considered to be complicated when the kidneys are affected, with clinical characteristics associated with other diseases such as tumors, with metabolic causes, or kidney failure. Moreover, urinary infections in men are classified as at risk of complication as they are nearly always linked to an anatomical cause.

Urinary infections in the general population are generally caused by a single microorganism: the pathogen *Escherichia coli* in more than 80% of urinary infections. In 10 to 15% of infections, it is the pathogen *Staphylococcus saprophyticus* that is responsible.

Antibiotic resistance in particular in uropathogenic strains of *Escherichia coli* (UPEC) is increasing and is worrying. This prompts scientists and healthcare professionals to identify new therapeutic strategies. Thus, the use of natural solutions, without undesirable effects, is presented as an alternative solution to antibiotics.

For example, Alkil et al. (Pediatr. Nephrol, 2006) evaluated the effect of oral administration of *Saccharomyces cerevisiae* var. *boulardii* on the total number of *E. coli* colonies in the colon of children. It was demonstrated that the administration of *S. boulardii* made it possible *E. coli* colonies to decrease significantly in the colon while significantly increasing the number of colonies of *S. boulardii*. The authors conclude that *S. boulardii* may be effective for reducing the total number of *E. coli* colonies in the stool. However, it is not stated whether this yeast has an effect on the prevention of urinary infections.

There is therefore a real need for new natural solutions for preventing urinary infections.

SUMMARY

The applicant has thus demonstrated, surprisingly, that the use of yeasts made it possible to prevent the occurrence of cystitis.

Thus, according to a first aspect of the invention, the present invention relates to a composition comprising at least one yeast for use in the prevention of simple cystitis and/or recurrent cystitis, the yeast being in the form of live or dead yeast, in the form of yeast derivatives such as yeast cell walls and the purified fractions of yeast cell walls, or mixtures thereof.

The inventors have also developed, according to a second aspect of the invention, a dietary supplement or a food composition comprising at least one yeast for use in the prevention of simple cystitis and/or recurrent cystitis, the yeast being in the form of live or dead yeast, in the form of yeast derivatives such as yeast cell walls and the purified fractions of yeast cell walls, or mixtures thereof.

According to a third aspect, the invention relates to a medical device comprising a composition comprising at least one yeast, for use thereof in the prevention of simple cystitis and/or recurrent cystitis, the yeast being in the form of live or dead yeast, in the form of yeast derivatives such as yeast cell walls and the purified fractions of yeast cell walls, or mixtures thereof.

BRIEF DESCRIPTION OF THE FIGURES

FIG. 1 shows the quantity in CFU of the UPEC strain in the intestinal sections for each of the groups tested.

FIG. 2 shows the bacterial load in CFU/mL (Log 10) in the urine for each test group.

FIG. 3 shows the bacterial load in CFU/mL (Log 10) in the bladder for each test group.

FIG. 4 shows the bacterial load in CFU/mL (Log 10) in the kidneys for each test group.

DETAILED DESCRIPTION

The present invention relates to a composition comprising at least one yeast for use in the prevention of simple cystitis and/or recurrent cystitis.

"Simple cystitis" means a urinary infection that is not at risk of complication. This only relates to women without a risk factor in the presence of only the characteristic symptoms of cystitis such as an urgent or more frequent need to urinate, a burning sensation, or tingling, without fever.

"Recurrent cystitis" means a succession of infectious episodes leading to simple cystitis. For it to be called "recurrent cystitis", the number of infectious episodes must be greater than or equal to four per year.

The term "yeast" denotes a yeast strain, a yeast obtained by culture of the yeast strain, the yeast being in the live or dead form, and in the form of yeast derivatives such as yeast cell walls and the purified fractions of yeast cell walls, or mixtures thereof.

The expression "yeast strain" denotes a relatively homogenous population of yeast cells obtained by culture (or multiplication) of the starting strain.

A yeast strain is obtained starting from a clone, a clone being a population of yeast cells obtained starting from a single yeast cell.

Culture of a yeast strain may be carried out by any suitable method. Methods for culture of yeast are known in the prior art, and a person skilled in the art knows how to optimize the culture conditions for each strain as a function of its nature. A yeast is obtained by multiplication of a yeast strain in a culture medium, for example as described in the reference book "Yeast Technology", 2nd edition, 1991, G. Reed and T. W. Nagodawithana, published by Van Nostrand Reinhold, ISBN 0-442-31892-8.

Thus, for example, on an industrial scale, yeast cells usable in the context of the present invention may be obtained by a method comprising the following steps:

culturing a yeast strain in a culture medium in several stages, firstly in semi-anaerobiosis, then in aerobiosis (oxygen-rich medium/atmosphere) to obtain multiplication of the starting yeast cells; and separating, by centrifugation, the yeast cells thus produced to obtain a liquid yeast cream containing between 12% and 25% of yeast dry matter.

The yeast so obtained is a live yeast. A live yeast or active yeast denotes a population of yeast cells whose metabolism is active.

In the context of the present invention, the live yeast is in the form of a dry yeast. A dry yeast is characterized by a low water content, and generally comprises a level of yeast dry matter above 90%, preferably a level of dry matter between 93% and 96%. One of the advantages of a dry yeast is long shelf life.

Thus, the method of production of yeast cells may further comprise a subsequent step of drying the cells, to obtain a yeast in the dry form. Drying may for example be drying by lyophilization, fluidized bed drying, drum drying or spray-drying.

According to another embodiment, the yeast strain is used in the form of dead yeast. A dead yeast may also be called "deactivated yeast" or "inactive yeast" or "inactivated yeast". It is a yeast whose metabolism has stopped permanently.

A dead yeast may be obtained by techniques that are familiar to a person skilled in the art, such as a heat treatment of yeast, a treatment consisting of subjecting the yeast to several cycles of freezing and successive thawing, treatment by irradiation, treatment by atomization or a combination of these treatments. An inactive yeast is generally in the dry form.

In another embodiment, it is a derivative of yeast cells that is used in the context of the present invention. This derivative is selected from yeast cell walls and the purified fractions of yeast cell walls.

The yeast cell walls correspond to the insoluble fraction of the yeast cells, i.e. the wall and the plasma membrane of the yeast cells.

Conventionally, the yeast cell walls are obtained by a method comprising a step of autolysis or of enzymatic hydrolysis of the yeast cells followed by a step of separating the soluble fraction from the insoluble fraction, the insoluble fraction isolated corresponding to the yeast cell walls and the soluble fraction corresponding to the yeast extracts. The insoluble fraction may then be dried. The yeast cell walls may be in liquid form, in dry form or in viscous form. They are considered to be in the dry form when their content of dry matter is at least 85%. Conversely, if their content of dry matter is less than 20 wt %, they are considered to be in the liquid form. Starting from 20 wt % and below 85 wt % of dry matter, the yeast cell walls are considered to be in the viscous form. The yeast cell walls are preferably used in the dry form. The method of obtaining the yeast cell walls is such that it preserves the structural polysaccharides of the cell wall, i.e. the β-glucans and the mannans, these mannans being in the form of mannoproteins. Methods of obtaining yeast cell walls are known in the prior art (see for example the reference work "Yeast Technology", 2nd edition, 1991, G. Reed and T. W. Nagodawithana, published by Van Nostrand Reinhold, New York, ISBN 0-442-31892-8).

The purified fractions of the yeast cell walls therefore relate in particular to glucans and mannans.

The mannoproteins and the glucans are obtained by conventional methods that are familiar to a person skilled in the art. Their extraction from the cell walls may be carried out by selective dissolution, or by chemical, enzymatic, or physicochemical hydrolysis.

In particular, the term "cell wall β-glucans" denotes the β-glucans of the wall of the yeast cells, which are essentially glucose polymers whose glucose units of the main chain are joined together by β-1,3 bonds and whose branches are joined together by β-1,6 bonds. The yeast β-glucans are insoluble and are of low viscosity. A person skilled in the art knows how to extract the β-glucans from the wall of the yeast cells. A common method comprises successive hot extractions with a base and with an acid (such as acetic acid), followed by water washing operations to remove any soluble compound of the yeast cell walls, and recovery of the insoluble material, consisting of the cell wall β-glucans.

The term "cell wall mannoproteins" denotes yeast polysaccharides and more precisely copolymers of neutral or acid monosaccharides (with 5 or 6 carbon atoms), bound together by glycosidic bonds and bound to proteins. In the yeast cell walls, the glucans constitute a network on which other glucans, chitin, and the mannoproteins are bound covalently. The mannoproteins are fixed to the glucans via a glycosyl phosphate containing a chain of 5 mannose residues. A person skilled in the art knows how to extract the mannoproteins from the wall of the yeast cells. A common method comprises enzymatic digestion of the yeast cell walls with a preparation of β-glucanases, followed by separation of the hydrolyzate by centrifugation, and purification by ultrafiltration. Another method is based on hot chemical extraction.

The present invention thus relates to a composition comprising at least one yeast according to the invention for use thereof in the prevention of simple cystitis and/or recurrent cystitis. The yeast according to the invention is selected from a live yeast, a dead yeast, yeast cell walls, purified fractions of yeast cell walls or mixtures thereof. Without wanting to be bound by any theory, the present inventors are of the opinion that the administration of a yeast according to the invention would make it possible to modulate the virulence factors of the pathogen, leading to a reduction of its pathogenicity. Moreover, the inventors think that yeast-pathogen co-aggregation would be involved, thus promoting elimination of the pathogen.

According to a preferred embodiment of the invention, simple and/or recurrent cystitis is cystitis induced by uropathogenic *Escherichia coli* bacteria (UPEC).

Surprisingly, the inventors have discovered that the administration of a composition comprising the yeast according to the invention had the effect of reducing carrying of UPEC in the urinary tract, as will be demonstrated in the examples.

The term "carrying" denotes the presence and/or multiplication of a pathogen at the level of an anatomical site that it is colonizing or infecting.

According to another preferred embodiment of the invention, the yeast according to the invention is selected from the yeasts of the genus *Saccharomyces*, and in particular the yeast is the yeast *Saccharomyces cerevisiae*.

According to a preferred embodiment of the invention, the yeast is obtained by culturing the *Saccharomyces cerevisiae* strain deposited on 17 Oct. 2007 in accordance with the Budapest Treaty with the National Collection of Cultures of Microorganisms (Collection Nationale de Cultures de Microorganismes, CNCM), Institut Pasteur, 25 rue du Docteur Roux, 75724 Paris cedex 15, under number I-3856.

This *Saccharomyces cerevisiae* yeast strain has been described previously, by the present applicant, in document WO 2009/103884, where it is described as being useful in the prevention and/or treatment of intestinal diseases, disorders or troubles; as well as in document WO 2014/009656, where it is described as being useful in the prevention and/or treatment of vaginal mycoses and in particular vaginal or vulvovaginal candidosis.

According to a preferred embodiment of the invention, the yeast is obtained by culturing the *Saccharomyces cerevisiae* strain deposited on 21 Aug. 2007 in accordance with the Budapest Treaty with the National Collection of Cultures of Microorganisms (CNCM), Institut Pasteur, 25 rue du Docteur Roux, 75724 Paris cedex 15, under number I-3799.

This strain *Saccharomyces cerevisiae* var. *boulardii* has been described previously, by the present applicant, in document WO 2009/103884, where it is presented as being useful in the prevention and/or treatment of intestinal diseases, disorders or troubles.

The microbiota corresponds to all of the microorganisms populating a microbiome, a specific environment. There are not one, but several microbiotas, whose composition varies depending on the region of the body. Its composition varies for example as a function of the aerobic or anaerobic medium, as a function of the acidity of the microbiome, as a function of the dryness or water content of the medium, or whether or not it is a fatty region. Thus, a distinction is made between the cutaneous microbiota, the vaginal microbiota, the urinary microbiota, the respiratory microbiota, the ORL microbiota and the intestinal microbiota, which is the largest. It is therefore important to bear in mind that the pathogens implicated in diseases of the urinary tract and those of the vaginal mucosa or intestinal mucosa are different. Thus, the behavior of pathogens and of probiotics with respect to the vaginal mucosa or intestinal mucosa is not transferrable to that adopted with respect to the urinary tract, since the environment of these mucosae is different.

According to a particular embodiment of the invention, the yeast according to the invention is in the form of dry yeast.

According to another embodiment of the invention, the composition comprising at least one yeast for use in the prevention of simple and/or recurrent cystitis is intended for oral or local administration.

The present invention relates in particular to the composition as defined above, for use thereof in the prevention of simple and/or recurrent cystitis, characterized in that the composition is in the form of hard capsule, pastille, pill, tablet, soft capsule, powder, suspension, liquid solution, granules, pessary, gel or cream. A person skilled in the art is able to select the most suitable vehicles and excipients for preparing a given type of formulation.

A composition according to the invention may further comprise additives such as preservatives, sweeteners, flavorings, thickening agents, colorants, moistening agents, disintegrants, absorption accelerators, lubricants, etc.

The present invention further relates to a composition as defined above, for use thereof in the prevention of simple cystitis and/or recurrent cystitis, characterized in that the composition is a food composition or a dietary supplement.

"Food composition" denotes any foodstuff, drink, or confectionery.

The food composition may for example be a drink, a cereal bar, a chewing gum, or a milk product.

"Dietary supplement" means a foodstuff that has the aim of supplementing the normal diet and that constitutes a concentrated source of nutrients or of other substances having a nutritional or physiological effect, alone or combined.

A dietary supplement is marketed in a dosage form, for example the dosage forms such as capsule, pastille, tablet, pill and other similar forms, sachet of powder, ampule of liquid, bottle provided with a dropper and other similar forms of liquid or powder preparations intended to be taken in measured units of a small amount.

The present invention also relates to a composition as defined above for use thereof in the prevention of simple cystitis and/or recurrent cystitis, characterized in that it further comprises another active ingredient.

The other active ingredient is plant-based, selected from an extract of cranberry, bilberry, red cranberry, arbutus, heather or mixtures thereof when the composition is intended for oral use.

In a particular embodiment of the invention, the other active ingredient is not a yeast.

The present invention further relates to a medical device, characterized in that it comprises a composition as described above, for use thereof in the prevention of simple and/or recurrent cystitis.

According to an advantageous embodiment of the invention, the medical device is a tampon or a sanitary napkin, a cream, a gel, a pessary, a tablet, a capsule, a pastille, a pill and other similar forms.

The present invention will now be illustrated with the figures and examples given hereunder, which are given for purposes of illustration, and are not in any way limiting.

EXAMPLES

Example 1: Tests of Co-Aggregation of Yeasts with UPEC Strains

Materials and Methods

UPEC Strains

Two uropathogenic *E. coli* strains are used in the present example, and were isolated from a midstream urine sample.

The first *E. coli* strain used, called UPEC1, is sensitive to all antibiotics.

The second *E. coli* strain used, called UPEC2, is multiresistant to antibiotics.

Growth Conditions of the UPEC Strains

The *Escherichia coli* strains are cultured overnight at 37° C. on Mueller-Hinton agar before the tests. The strains are then collected by centrifugation for 5 minutes at 11000 rpm, washed twice with a sterile solution of phosphate-buffered saline (PBS), the concentration being adjusted to the desired concentration, and resuspended in the same buffer.

Yeasts Tested

The yeasts tested for each of the two UPEC strains are as follows:

- Inactive yeast *Saccharomyces cerevisiae* CNCM I-3856 (IY) having a dry matter content ≥94% and a pH between 5.5 and 6.3,
- Live yeast *Saccharomyces cerevisiae* CNCM I-3856 (GI) at a content $\geq 5.10^9$ CFU/g,
- Live yeast *Saccharomyces cerevisiae* var. *boulardii* CNCM I-3799 (SCB) at a content $\geq 2.10^{10}$ CFU/g,
- Cell wall glucans (WG) having a level of beta-glucans ≥50%.

Before the tests, the yeasts are rehydrated with PBS buffer.

Co-Aggregation Protocol

The UPEC strains ($1\times10^9$ cells/mL) in PBS buffer solution are added at a volume equal to that of the yeast (10 mg/mL).

This mixture is vortexed for at least 10 seconds and deposited in a 24-well plate for 4 hours at 37° C. with stirring, at a rate of 1 mL per well.

The suspension is then observed in an inverted transmitted light microscope to evaluate the degree of aggregation and to give a score according to the following scale:

0=no aggregation

1=small aggregates comprising small visible clusters

2=aggregates comprising a larger number of microorganisms, established at the center of the well 3=macroscopically visible cluster comprising larger groups established at the center of the well 4=maximum score allocated for describing a large, macroscopically visible cluster at the center of the well.

In parallel, the capacity for self-aggregation of the different yeasts with one another is also tested according to the same protocol given above but without adding UPEC strains to the mixture. The yeasts are tested individually.

Results

The results are from 3 tests that are independent of one another, each of the tests being out carried with duplicate samples (dp hereinafter).

The results of the self-aggregation and co-aggregation tests are given in Tables 1 and 2 below.

TABLE 1

| Essais | dp | UPEC1 | IY | GI | SCB | WG | UPEC1 + IY | UPEC1 + GI | UPEC1 + SCB | UPEC1 + WG |
|---|---|---|---|---|---|---|---|---|---|---|
| 1 | 1 | 0 | 4 | 0 | 1 | 4 | 3 | 3 | 4 | 4 |
| | 2 | 0 | 4 | 0 | 1 | 4 | 3 | 3 | 4 | 4 |
| 2 | 1 | 0 | 4 | 0 | 1 | 4 | 3 | 3 | 4 | 4 |
| | 2 | 0 | 4 | 0 | 1 | 4 | 3 | 3 | 4 | 4 |
| 3 | 1 | 0 | 4 | 0 | 1 | 4 | 3 | 4 | 4 | 4 |
| | 2 | 0 | 4 | 0 | 1 | 4 | 3 | 4 | 4 | 4 |
| Score moyen | | 0 | 4 | 0 | 1 | 4 | 3 | 3.33 | 4 | 4 |

Results of the self-aggregation and co-aggregation tests between UPEC1 and the yeasts

| Source | Translation |
|---|---|
| Essais | Tests |
| Score moyen | Average score |

TABLE 2

| Essais | dp | UPEC2 | IY | GI | SCB | WG | UPEC2 + IY | UPEC2 + GI | UPEC2 + SCB | UPEC2 + WG |
|---|---|---|---|---|---|---|---|---|---|---|
| 1 | 1 | 0 | 4 | 0 | 1 | 4 | 3 | 4 | 4 | 4 |
| | 2 | 0 | 4 | 0 | 1 | 4 | 3 | 4 | 4 | 4 |
| 2 | 1 | 0 | 4 | 0 | 1 | 4 | 3 | 4 | 4 | 4 |
| | 2 | 0 | 4 | 0 | 1 | 4 | 3 | 4 | 4 | 4 |
| 3 | 1 | 0 | 4 | 0 | 1 | 4 | 2 | 4 | 4 | 4 |
| | 2 | 0 | 4 | 0 | 1 | 4 | 2 | 4 | 4 | 4 |
| Score moyen | | 0 | 4 | 0 | 1 | 4 | 2.66 | 4 | 4 | 4 |

Results of the self-aggregation and co-aggregation tests between UPEC2 and the yeasts

| Source | Translation |
|---|---|
| Essais | Tests |
| Score moyen | Average score |

Capacity for Self-Aggregation of the Yeasts and the UPEC Strains

The isolates of live yeast (GI), UPEC1 and UPEC2 are not capable of self-aggregating, the score obtained for each of these isolates being 0.

The isolates of *S. boulardii* (SCB) show a limited capacity for self-aggregation, the score obtained for these isolates being 1.

The isolates of inactive yeast (IY) and of cell wall glucans (WG) show strong self-aggregation, the score obtained for each of these isolates being 4.

Capacity of the Yeasts for Inducing Aggregation with the UPEC Strains

The isolates of IY, GI, SCB and WG are capable of aggregating the 2 isolates of *E. coli*, UPEC1 and UPEC2.

In particular, the isolate UPEC2 has a maximum co-aggregation score with GI, SCB and WG followed by IY with a slightly lower score (cf. Table 2). The isolate of UPEC1 has a maximum score with SCB, WG followed by GI and IY with a slightly lower score (cf. Table 1).

Conclusion

The capacity for inducing co-aggregation with *E. coli* may constitute an important phenomenon in establishing and maintaining a healthy urogenital flora and an important defense mechanism against urogenital infections.

The present example thus demonstrates that:

All the compounds tested are capable of inducing co-aggregation with the UPEC1 and UPEC2 strains The yeasts SCB and WG are capable of co-aggregating with UPEC1 and UPEC2 with a maximum score;

The yeasts GI and IY are capable of co-aggregating with UPEC1 and UPEC2.

Thus, probiotics can co-aggregate with strains that are multiresistant to antibiotics. There is therefore a real beneficial use of the yeasts, partially replacing or supplementing antibiotic therapy as an aid during treatment of urinary infections that are multiresistant to antibiotics.

Example 2: Evaluation of the Effect of Yeasts on Colonization of the Murine Intestine by a Uropathogenic Strain Materials and Methods Murine Model The animal model used is a female mouse of the BALB/CYJ line, aged 7 weeks. The mice are housed in groups of 5 on a ventilated support.

Uropathogenic Strain

The uropathogenic strain used in the example is a uropathogenic strain of *E. coli* that is multiresistant to antibiotics, called UPEC3 hereinafter.

Yeasts Tested

The yeasts tested are as follows:

Inactive yeast *Saccharomyces cerevisiae* CNCM I-3856 (IY) having a dry matter content ≥94% and a pH between 5.5 and 6.3, Live yeast *Saccharomyces cerevisiae* CNCM I-3856 (GI) at a content ≥5.10$^9$ CFU/g.

Protocol

On D (=Day) −2, the feces are collected and streptomycin sulfate (5 mg/mL) is added to the drinking water for 2 days to decrease the resident aerobic/anaerobic bacteria. The feces are collected by placing each animal in empty cages for the time it takes to collect 2 to 4 fecal pellets, which are then transferred to pre-weighed 2 mL sterile tubes. The tubes are then weighed and the fecal samples are resuspended in 1 mL of PBS, series-diluted to 1:10, and deposited on dishes of Drigalski agar medium with addition of 100 μg/ml of streptomycin and of kanamycin.

D=0, inoculation of the UPEC3 strain

Before bacterial inoculation, the feces of the mice are collected to verify absence of enterobacteria that are resistant to streptomycin and to kanamycin.

The inoculation of the UPEC3 strain is carried out by oral gavage at a dose of 1××10$^7$ CFU. The inoculum is obtained from an overnight culture in LB ("Lysogeny Broth") liquid medium, and then diluted in 200 μL of sodium bicarbonate solution.

At the same time, the drinking water was replaced with an aqueous solution of 1 mg/mL of kanamycin sulfate for 2 days.

D=1, start of the experimental treatment administered daily by gavage, as follows:

Group 1 (control): 10 mice distributed in 2 cages receive 200 μL of PBS;

Group 2 (IY): 10 mice distributed in 2 cages receive 1 mg of the compound IY resuspended in 200 μL of PBS;

Group 3 (GI): 10 mice distributed in 2 cages receive 1 mg of the compound GI resuspended in 200 μL of PBS.

D=14, no treatment is administered.

The animals are sacrificed and dissected to remove the ileal intestinal sections and colon. During removal, the organs are emptied of their contents and washed in sterile PBS in aseptic conditions.

The weighed intestinal sections are homogenized in PBS in the gentle MACS™ Octo Dissociator and diluted from 10 to 10 in microtiter plates. An aliquot from each dilution is then deposited on a dish of Drigalsky agar medium with addition of 100 μg/mL of streptomycin and kanamycin for counting the adherent UPEC3 strains. Deposition is carried out in triplicate. Counting is carried out manually.

Results

One mouse from group 3 (GI) died on day 7 without precise cause but probably due to the stress of the repeated gavage.

An intestinal section of the colon of one mouse from group 2 (IY) was unusable.

FIG. 1 shows the quantity in CFU of the UPEC3 strain in the intestinal sections for each of the groups tested on day 14. (*$p<0.05$; ***$p<0.0001$)

A significant decrease is observed (Mann-Whitney test) in the quantity of the UPEC3 strain in the ileal section of the intestine for group 2 (IY).

A significant reduction is observed in the quantity of the UPEC3 strain in the colon for groups 2 (IY) and 3 (GI).

Conclusion

The level of adherent flora in the ileum and the colon is significantly higher in the control group than in the other two groups that received the yeasts. More precisely, it can be seen in the section of the colon that the two products lead to a significant reduction in the level of adherent UPEC3 strains, whereas in the ileal sections only the product IY has a significant effect. However, with the product GI, the effect in the ileal section is almost significant, since for 4 mice out of 9 the level of the adherent UPEC3 strains reached the threshold of detection.

The two products, live yeast and inactive yeast, therefore display the capacity to reduce the level of the uropathogenic strain of *E. coli* adhering to the intestinal epithelium.

Thus, these two yeasts are capable of compromising maintenance of the intestinal reservoir of the UPEC3 strain.

Example 3: Evaluation of the Anti-Infectious Efficacy of a Yeast

Materials and Methods

*E. coli* Strain

A uropathogenic *Escherichia coli* strain, called UPEC4 in the present example, is used.

Compounds Tested

Buffer

The buffer solution used is a PBS 1× buffer solution.

Yeast

The yeast evaluated is the live yeast *Saccharomyces cerevisiae* CNCM I-3856 in the dry form, called GI hereinafter. Before rehydration, the yeast is in the dry form and has a content ≥5.10$^9$ CFU/g. Before the tests, the yeast is rehydrated with PBS buffer.

Tobramycin

Tobramycin is used as it is a powerful antibiotic and a reference medicinal product. Before the tests, tobramycin is suspended with PBS buffer.

Animal Model

The animal model used is a female mouse of the C57BL/6J line, aged 8 weeks. The mice are housed in groups of 5 on litter of wood shavings at a temperature of about 22° C.

They are fed with a standard complete maintenance diet such as SAFE A04® for rats and mice and have access to water ad libitum.

Test Groups 10 female mice per group are used (except group 1, only 5 females), aged 8 weeks.

The groups tested are as follows:

G1: mouse+UPEC4+buffer=control;

G2: mouse+UPEC4+tobramycin (30 mg/kg)=positive control;

G3: mouse+UPEC4+GI (13.5 mg/kg).

Protocols

Administration of the Test Compounds

The compounds are administered locally (transurethral administration), 24 hours and 1 hour before infection for groups 1 and 3. Tobramycin, the reference medicinal product, is administered intraperitoneally 1 hour before infection in group 3.

Infecting the Mice with UPEC4

The mouse is first anesthetized with isoflurane (3%). The urine is evacuated from the bladder before infection. Then the mouse is infected with 50 μL of UPEC4 (administered in 2-3 seconds), i.e. administration of $6\times10^7$ CFU (colony forming units) of UPEC4 by the transurethral route.

Infection by the transurethral route is carried out by inserting sterilized polyethylene tube (internal dimension 0.28 mm, external dimension 0.61 mm) attached to a 30 G hypodermic needle in the urethra.

20 hours after infection, urine samples are collected from each mouse. The bladder and the kidneys are removed and homogenized for the CFU count.

Sample Preparation for Determining the Bacterial Load (CFU)

The animals are sacrificed 20 hours after inoculation of the UPEC strain by inhalation of $CO_2$. The right kidney and half of the bladder are homogenized in sterile isotonic saline solution using the Dispomix® homogenization system for single sterile use. Serial dilutions at 1/10 of the samples (urine, kidney and bladder homogenate) are effected with isotonic saline solution. An aliquot of 10 μl of each dilution is then deposited on a dish of BHI ("Brain Heart Infusion") agar medium. Deposition is carried out in duplicate. The Petri dish is then incubated overnight at 37° C. in order to determine the number of viable bacteria in CFU. Counting is carried out manually by two experimenters.

Statistical Analysis of the Results

Before beginning statistical analysis, the Agostino and Pearson test was performed in order to determine whether the variables follow the normal law.

Statistical evaluation of the differences between the experimental groups is performed using parametric tests (one-factor ANOVA followed by a Dunnett post-hoc test, for normally distributed data) or nonparametric (Kruskal Wallis followed by a multiple comparison of the Dunn test for an abnormal distribution) depending on the results of the test for normality.

The Grubb test is used for determining whether one of the values in the group is a significant aberrant value.

The values are expressed as the mean value±SEM. A value of $P\leq0.05$ is regarded as statistically significant.

Results

FIG. 2 shows the bacterial load in CFU in the urine for each of the groups tested (n.s: not significant, *$p<0.05$, ***$p<0.001$ for G2 and G3 compared to G1).

A significant decrease in CFU in the urine is observed in the mice infected with UPEC4 and treated with GI (group 3) and tobramycin (group 2) relative to the mice in group 1 infected with UPEC4.

FIG. 3 shows the bacterial load in CFU in the bladder for each of the groups tested (n.s: not significant, *$p<0.05$, ***$p<0.001$ for G2 and G3 compared to G1).

A significant decrease in CFU in the bladder is observed in the mice infected with UPEC4 and treated with GI (group 3) and tobramycin (group 2) relative to the mice in group 1 infected with UPEC4.

FIG. 4 shows the bacterial load in CFU in the kidneys for each of the groups tested (n.s: not significant, *$p<0.05$, ***$p<0.001$ for G2 and G3 compared to G1).

A significant decrease in CFU in the kidneys is observed in the mice infected with UPEC4 and treated with GI (group 3) and tobramycin (group 2) relative to the mice in group 1 infected with UPEC4.

Conclusion

In the mouse model the UPEC4 strain induces a significant increase in the bacterial load.

Local administration of the live yeast *Saccharomyces cerevisiae* CNCM I-3856 in mice infected with a UPEC4 strain induces a significant decrease in the bacterial load in the urine, bladder, and kidneys.

Infection of the urinary tract with the uropathogenic *Escherichia coli* strain is therefore inhibited very actively by local administration of the live yeast *Saccharomyces cerevisiae* CNCM I-3856.

The invention claimed is:

1. A method of preventing simple cystitis in a woman infected by uropathogenic *Escherichia coli* bacteria, comprising administering to said woman an effective amount of a composition that prevents simple cystitis by reducing a presence and/or multiplication of uropathogenic *Escherichia coli* bacteria in said subject's urinary tract, said composition comprising an active ingredient, wherein the active ingredient of the composition consists of a yeast selected from the group consisting of a live yeast, a dead yeast, yeast cell walls, purified yeast cell walls and mixtures thereof, said yeast being obtained by culture of either a *Saccharomyces cerevisiae* strain deposited with the CNCM on 17 Oct. 2007 under number I-3856 or a *Saccharomyces cerevisiae* var. *boulardii* strain deposited with the CNCM on 21 Aug. 2007 under number I-3799, wherein said simple cystitis is induced by uropathogenic *Escherichia coli* bacteria infecting a urinary tract.

2. The method as claimed in claim 1, wherein the yeast is in the form of dry yeast.

3. The method as claimed in claim 1, wherein the composition is administered to the woman by local or oral administration.

4. The method as claimed in claim 1, wherein the composition is in the form of a hard capsule, pill, pastille, tablet, soft capsule, powder, suspension, liquid solution, granules, pessary, gel or cream.

5. The method as claimed in claim 1, wherein the composition is a food composition or a dietary supplement.

6. A method of preventing simple cystitis in a woman infected by uropathogenic *Escherichia coli* bacteria, comprising administering to said woman by oral administration an effective amount of a composition comprising active ingredients, wherein the active ingredients of the composition consist of:

a yeast selected from the group consisting of a live yeast, a dead yeast, yeast cell walls, purified yeast cell walls and mixtures thereof, said yeast being obtained by culture of either a *Saccharomyces cerevisiae* strain deposited with the CNCM on 17 Oct. 2007 under number I-3856 or a *Saccharomyces cerevisiae* var. *boulardii* strain deposited with the CNCM on 21 Aug. 2007 under number I-3799, and an extract selected from the group consisting of an extract of cranberry, an extract of bilberry, an extract of arbutus, an extract of red cranberry, an extract of heather and mixtures thereof, wherein said simple cystitis is induced by uropathogenic *Escherichia coli* bacteria infecting a urinary tract.

7. The method as claimed in claim 6, wherein the yeast is in the form of dry yeast.

8. The method as claimed in claim 6, wherein the composition is in the form of a hard capsule, pill, pastille, tablet, soft capsule, powder, suspension, liquid solution, and granules.

9. The method as claimed in claim 6, wherein the composition is a food composition or a dietary supplement.

10. A method of inhibiting a uropathogenic *Escherichia coli* infection in a urinary tract in a subject, comprising administering to a subject infected with uropathogenic *Escherichia coli* an effective amount of a composition that reduces a presence and/or multiplication of uropathogenic *Escherichia coli* bacteria in the urinary tract of said subject, said composition comprising an active ingredient, wherein the active ingredient of the composition consists of a yeast selected from the group consisting of a live yeast, a dead yeast, yeast cell walls, purified yeast cell walls and mixtures thereof, said yeast being obtained by culture of either a *Saccharomyces cerevisiae* strain deposited with the CNCM on 17 Oct. 2007 under number I-3856 or a *Saccharomyces cerevisiae* var. *boulardii* strain deposited with the CNCM on 21 Aug. 2007 under number I-3799.

* * * * *